(12) United States Patent
Lynch et al.

(10) Patent No.: US 9,790,147 B2
(45) Date of Patent: *Oct. 17, 2017

(54) HYDROCARBON PROCESSING

(71) Applicants: Ortloff Engineers, Ltd., Midland, TX (US); S.M.E. Products, LP, Houston, TX (US)

(72) Inventors: Joe T Lynch, Midland, TX (US); John D. Wilkinson, Midland, TX (US); Scott A. Miller, Midland, TX (US); Hank M. Hudson, Midland, TX (US); Kyle T. Cuellar, Katy, TX (US); Andrew F. Johnke, Beresford, SD (US); W. Larry Lewis, Tomball, TX (US)

(73) Assignees: Ortloff Engineers, Ltd., Midland, TX (US); S.M.E. Products, LP, Houston, TX (US)

( * ) Notice: Subject to any disclaimer, the term of this patent is extended or adjusted under 35 U.S.C. 154(b) by 357 days.

This patent is subject to a terminal disclaimer.

(21) Appl. No.: 14/462,069

(22) Filed: Aug. 18, 2014

(65) Prior Publication Data

US 2015/0073195 A1 Mar. 12, 2015
US 2015/0315105 A2 Nov. 5, 2015

Related U.S. Application Data

(60) Provisional application No. 61/879,237, filed on Sep. 18, 2013, provisional application No. 61/878,977, (Continued)

(51) Int. Cl.
*C07C 7/04* (2006.01)
*B01D 3/16* (2006.01)
(Continued)

(52) U.S. Cl.
CPC .............. *C07C 7/04* (2013.01); *B01D 3/16* (2013.01); *B01D 3/32* (2013.01); *B01D 3/322* (2013.01);
(Continued)

(58) Field of Classification Search
None
See application file for complete search history.

(56) References Cited

U.S. PATENT DOCUMENTS

| 33,408 A | 10/1861 | Turner et al. |
| 311,402 A | 1/1885 | Withington |

(Continued)

OTHER PUBLICATIONS

Supplemental Notice of Allowability issued in U.S. Appl. No. 12/689,616, dated Feb. 10, 2015 (12 pages).
(Continued)

*Primary Examiner* — Tam M Nguyen
(74) *Attorney, Agent, or Firm* — Fitzpatrick, Cella, Harper & Scinto (57) ABSTRACT

A process and an apparatus are disclosed for a compact processing assembly to fractionate lighter components from mixed hydrocarbon streams. The hydrocarbon stream is supplied to the processing assembly between an absorbing means and a mass transfer means. A distillation vapor stream is collected from the upper region of the absorbing means and cooled in a first heat and mass transfer means inside the processing assembly to partially condense it, forming a volatile stream and a condensed stream. The condensed stream is supplied to the absorbing means as its top feed. A distillation liquid stream is collected from the lower region of the mass transfer means and heated in a second heat and mass transfer means inside the processing assembly to strip out its volatile components, forming a relatively less volatile stream and a vaporized stream. The vaporized stream is supplied to the mass transfer means as its bottom feed.

8 Claims, 9 Drawing Sheets

Related U.S. Application Data filed on Sep. 17, 2013, provisional application No. 61/876,409, filed on Sep. 11, 2013.

(51) Int. Cl.

| | |
|---|---|
| *B01D 3/32* | (2006.01) |
| *B01D 3/42* | (2006.01) |
| *F25J 1/00* | (2006.01) |
| *B01D 5/00* | (2006.01) |
| *C10L 3/06* | (2006.01) |
| *C10L 3/12* | (2006.01) |
| *C10G 7/08* | (2006.01) |

(52) U.S. Cl.
CPC ............ *B01D 3/42* (2013.01); *B01D 5/0063* (2013.01); *C10G 7/08* (2013.01); *C10L 3/06* (2013.01); *C10L 3/12* (2013.01); *F25J 1/0022* (2013.01); *C10L 2290/06* (2013.01); *C10L 2290/24* (2013.01); *C10L 2290/541* (2013.01); *C10L 2290/543* (2013.01)

(56) References Cited

U.S. PATENT DOCUMENTS

| | | | |
|---|---|---|---|
| 3,292,380 A | 12/1966 | Bucklin | |
| 3,292,980 A | 12/1966 | Gustafsson et al. | |
| 3,477,915 A | 11/1969 | Gantt et al. | |
| 3,508,412 A | 4/1970 | Yearout | |
| 3,516,261 A | 6/1970 | Hoffman | |
| 3,625,017 A | 12/1971 | Hoffman | |
| 3,797,261 A | 3/1974 | Juncker et al. | |
| 3,983,711 A | 10/1976 | Solomon | |
| 4,061,481 A | 12/1977 | Campbell et al. | |
| 4,127,009 A | 11/1978 | Phillips | |
| 4,140,504 A | 2/1979 | Campbell et al. | |
| 4,157,904 A | 6/1979 | Campbell et al. | |
| 4,171,964 A | 10/1979 | Campbell et al. | |
| 4,185,978 A | 1/1980 | McGalliard et al. | |
| 4,251,249 A | 2/1981 | Gulsby | |
| 4,278,457 A | 7/1981 | Campbell et al. | |
| 4,519,824 A | 5/1985 | Huebel | |
| 4,617,039 A | 10/1986 | Buck | |
| 4,687,499 A | 8/1987 | Aghili | |
| 4,688,399 A | 8/1987 | Reimann | |
| 4,689,063 A | 8/1987 | Paradowski et al. | |
| 4,690,702 A | 9/1987 | Paradowski et al. | |
| 4,854,955 A | 8/1989 | Campbell et al. | |
| 4,869,740 A | 9/1989 | Campbell et al. | |
| 4,889,545 A | 12/1989 | Campbell et al. | |
| 5,255,528 A | 10/1993 | Dao | |
| 5,275,005 A | 1/1994 | Campbell et al. | |
| 5,282,507 A | 2/1994 | Tongu et al. | |
| 5,316,628 A | 5/1994 | Collin et al. | |
| 5,335,504 A | 8/1994 | Durr et al. | |
| 5,339,654 A | 8/1994 | Cook et al. | |
| 5,367,884 A | 11/1994 | Phillips et al. | |
| 5,410,885 A | 5/1995 | Smolarek et al. | |
| 5,555,748 A | 9/1996 | Campbell et al. | |
| 5,566,554 A | 10/1996 | Vijayaraghavan et al. | |
| 5,568,737 A | 10/1996 | Campbell et al. | |
| 5,675,054 A | 10/1997 | Manley et al. | |
| 5,685,170 A | 11/1997 | Sorensen | |
| 5,713,216 A | 2/1998 | Erickson | |
| 5,771,712 A | 6/1998 | Campbell et al. | |
| 5,799,507 A | 9/1998 | Wilkinson et al. | |
| 5,881,569 A | 3/1999 | Campbell et al. | |
| 5,890,377 A | 4/1999 | Foglietta | |
| 5,890,378 A | 4/1999 | Rambo et al. | |
| 5,942,164 A | 8/1999 | Tran | |
| 5,983,664 A | 11/1999 | Campbell et al. | |
| 6,077,985 A | 6/2000 | Stork | |
| 6,182,469 B1 | 2/2001 | Campbell et al. | |
| 6,361,582 B1 | 3/2002 | Pinnau et al. | |
| 6,516,631 B1 | 2/2003 | Trebble | |
| 6,565,626 B1 | 5/2003 | Baker et al. | |
| 6,578,379 B2 | 6/2003 | Paradowski | |
| 6,694,775 B1 | 2/2004 | Higginbotham et al. | |
| 6,712,880 B2 | 3/2004 | Fogietta et al. | |
| 6,742,358 B2 | 6/2004 | Wilkinson et al. | |
| 6,915,662 B2 | 7/2005 | Wilkinson et al. | |
| 6,945,075 B2 | 9/2005 | Wilkinson et al. | |
| 7,010,937 B2 | 3/2006 | Wilkinson et al. | |
| 7,165,423 B2 | 1/2007 | Winningham | |
| 7,191,617 B2 | 3/2007 | Cuellar et al. | |
| 7,204,100 B2 | 4/2007 | Wilkinson et al. | |
| 7,210,311 B2 | 5/2007 | Wilkinson et al. | |
| 7,219,513 B1 | 5/2007 | Mostafa | |
| 7,565,815 B2 | 7/2009 | Wilkinson et al. | |
| 7,631,516 B2 | 12/2009 | Cuellar et al. | |
| 7,713,497 B2 | 5/2010 | Mak | |
| 8,156,758 B2 | 4/2012 | Denton et al. | |
| 8,434,325 B2 | 5/2013 | Martinez et al. | |
| 8,590,340 B2 | 11/2013 | Pitman et al. | |
| 8,881,549 B2 | 11/2014 | Johnke et al. | |
| 8,919,148 B2 | 12/2014 | Wilkinson et al. | |
| 9,021,831 B2 | 5/2015 | Johnke et al. | |
| 9,021,832 B2 | 5/2015 | Pierce et al. | |
| 9,052,136 B2 | 6/2015 | Johnke et al. | |
| 9,052,137 B2 | 6/2015 | Johnke et al. | |
| 9,057,558 B2 | 6/2015 | Johnke et al. | |
| 9,068,774 B2 | 6/2015 | Johnke et al. | |
| 9,074,814 B2 | 7/2015 | Johnke et al. | |
| 9,080,810 B2 | 7/2015 | Pitman et al. | |
| 9,080,811 B2 | 7/2015 | Johnke et al. | |
| 2001/0008073 A1 | 7/2001 | Finn et al. | |
| 2002/0166336 A1 | 11/2002 | Wilkinson et al. | |
| 2004/0079107 A1 | 4/2004 | Wilkinson et al. | |
| 2004/0172967 A1 | 9/2004 | Patel et al. | |
| 2005/0229634 A1 | 10/2005 | Huebel et al. | |
| 2005/0247078 A1 | 11/2005 | Wilkinson et al. | |
| 2005/0268649 A1 | 12/2005 | Wilkinson et al. | |
| 2006/0032269 A1 | 2/2006 | Cellar et al. | |
| 2006/0086139 A1 | 4/2006 | Eaton et al. | |
| 2006/0283207 A1 | 12/2006 | Pitman et al. | |
| 2008/0000265 A1 | 1/2008 | Cuellar et al. | |
| 2008/0078205 A1 | 4/2008 | Cuellar et al. | |
| 2008/0190136 A1 | 8/2008 | Pitman et al. | |
| 2008/0271480 A1 | 11/2008 | Mak | |
| 2009/0100862 A1* | 4/2009 | Wilkinson ............ F25J 3/0209 62/620 |
| 2009/0107175 A1 | 4/2009 | Patel et al. | |
| 2009/0293538 A1 | 12/2009 | Wilkinson et al. | |
| 2010/0251764 A1 | 10/2010 | Johnke et al. | |
| 2010/0275647 A1 | 11/2010 | Johnke et al. | |
| 2010/0287983 A1 | 11/2010 | Johnke et al. | |
| 2010/0287984 A1 | 11/2010 | Johnke et al. | |
| 2010/0326134 A1 | 12/2010 | Johnke et al. | |
| 2011/0067441 A1 | 3/2011 | Martinez et al. | |
| 2011/0067442 A1 | 3/2011 | Martinez et al. | |
| 2011/0067443 A1 | 3/2011 | Martinez et al. | |
| 2011/0226011 A1 | 9/2011 | Johnke et al. | |
| 2011/0226013 A1 | 9/2011 | Johnke et al. | |
| 2011/0232328 A1 | 9/2011 | Johnke et al. | |
| 2015/0073194 A1 | 3/2015 | Hudson et al. | |
| 2015/0073196 A1 | 3/2015 | Miller et al. | |

OTHER PUBLICATIONS

Comments on Statement of Reasons for Allowance filed in U.S. Appl. No. 12/689,616, dated Mar. 3, 2015 (7 pages).
Response and Statement of Interview filed in U.S. Appl. No. 13/052,575, dated Mar. 16, 2015 (37 pages).
Response and Statement of Interview filed in U.S. Appl. No. 13/052,348, dated Mar. 17, 2015 (37 pages).
Response and Statement of Interview filed in U.S. Appl. No. 13/053,792, dated Mar. 18, 2015 (37 pages).
Response, Statement of Interview and Petition for Extension of Time filed in U.S. Appl. No. 13/051,682, dated Mar. 19, 2015 (37 pages).
Response, Statement of Interview and Petition for Extension of Time filed in U.S. Appl. No. 13/048,315, dated Mar. 20, 2015 (93 pages).

(56) References Cited

OTHER PUBLICATIONS

Amendment and Statement of Interview filed in U.S. Appl. No. 13/052,348, dated Mar. 26, 2015 (23 pages).
Amendment and Statement of Interview filed in U.S. Appl. No. 13/051,682, dated Mar. 26, 2015 (29 pages).
Amendment and Statement of Interview filed in U.S. Appl. No. 13/053,792, dated Mar. 26, 2015 (25 pages).
Amendment and Statement of Interview filed in U.S. Appl. No. 13/052,575, dated Mar. 26, 2015 (20 pages).
Notice of Allowance and Fee(s) Due issued in U.S. Appl. No. 12/689,616, dated Jan. 9, 2015 (15 pages).
Comments on Statement of Reasons for Allowance filed in U.S. Appl. No. 12/689,616, dated Jan. 30, 2015 (8 pages).
Office Action issued in U.S. Appl. No. 13/052,348, dated Dec. 17, 2014 (13 pages).
Office Action issued in U.S. Appl. No. 13/051,682, dated Dec. 18, 2014 (13 pages).
Office Action issued in U.S. Appl. No. 13/053,792, dated Dec. 18, 2014 (20 pages).
Office Action issued in U.S. Appl. No. 13/052,575, dated Dec. 16, 2014 (16 pages).
Advisory Action Before the Filing of an Appeal Brief issued in U.S. Appl. No. 12/689,616, dated Nov. 28, 2014 (3 pages).
Submission Under 37 C.F.R. § 1.114, Statement Of Interview, And Petition For Extension Of Time filed in U.S. Appl. No. 12/689,616, dated Dec. 8, 2014 (39 pages).
International Search Report and Written Opinion issued in International Application No. PCT/US2011/028872 dated May 18, 2011—7 pages.
International Search Report and Written Opinion issued in International Application No. PCT/US2011/29234 dated May 20, 2011—30 pages.
International Search Report and Written Opinion issued in International Application No. PCT/US2011/029034 dated Jul. 27, 2011—40 pages.
International Search Report and Written Opinion issued in International Application No. PCT/US2011/029409 dated May 17, 2011—15 pages.
International Search Report and Written Opinion issued in International Application No. PCT/US2011/029239 dated May 20, 2011—21 pages.
E. Ross Mowrey, "Efficient, High Recovery of Liquids From Natural Gas Utilizing a High Pressure Absorber," Proceedings of the Eighty-First Annual Convention of the Gas Processors Association, Dallas, Texas, Mar. 11-13, 2002.

"Dew Point Control Gas Conditioning Units," SME Products Brochure, Gas Processors Assoc. Conference (Apr. 5, 2009).
"Fuel Gas Conditioning Units for Compressor Engines," SME Products Brochure, Gas Processors Assoc. Conference (Apr. 5, 2009).
"P&ID Fuel Gas Conditioner," Drawing No. SMEP-901, Date Drawn: Aug. 29, 2007, SME, available at http://www.sme-llc.com/sme.cfm?a=prd&catID=58&subID=44&prdID=155 (Apr. 24, 2009).
"Fuel Gas Conditioner Preliminary Arrangement," Drawing No. SMP-1007-00, Date Drawn: Nov. 11, 2008, SME, available at http://www.sme-llc.com/sme.cfm?a=prd&catID=58&subID=44&prdID=155 (Apr. 24, 2009).
"Product: Fuel Gas Conditioning Units," SME Associates, LLC, available at http://www.smellc.com/sme.cfm?a=prd&catID=58&subID=44&prdID=155 (Apr. 24, 2009).
International Search Report and Written Opinion issued in International Application No. PCT/US2010/21364 dated Mar. 29, 2010—20 pages.
International Search Report and Written Opinion issued in International Application No. PCT/US2010/26185 dated Jul. 9, 2010—20 pages.
International Search Report and Written Opinion issued in corresponding International Application No. PCT/US2010/29331 dated Jul. 2, 2010—15 pages.
International Search Report and Written Opinion issued in International Application No. PCT/US2010/33374 dated Jul. 9, 2010—18 pages.
International Search Report and Written Opinion issued in International Application No. PCT/US2010/35121 dated Jul. 19, 2010—18 pages.
International Search Report and Written Opinion issued in International Application No. PCT/US2010/37098 dated Aug. 17, 2010—12 pages.
International Search Report and Written Opinion issued in International Application No. PCT/US14/51544 dated Nov. 24, 2014—16 pages.
Huebel, R., et al., "New NGL-Recovery Process Provides Viable Alternative", Oil & Gas Journal, Jan. 9, 2012 (9 pages).
International Search Report and Written Opinion issued in International Application No. PCT/US14/51547 dated Nov. 24, 2014—21 pages.
International Search Report and Written Opinion issued in International Application No. PCT/US14/51548 dated Nov. 25, 2014—24 pages.

\* cited by examiner

FIG. 9

HYDROCARBON PROCESSING

BACKGROUND OF THE INVENTION

This invention relates to a process and apparatus for the separation of a hydrocarbon stream. The applicants claim the benefits under Title 35, United States Code, Section 119(e) of prior U.S. Provisional Application No. 61/876,409 which was filed on Sep. 11, 2013, No. 61/878,977 which was filed on Sep. 17, 2013, and No. 61/879,237 which was filed on Sep. 18, 2013. Assignees S.M.E. Products LP and Ortloff Engineers, Ltd. were parties to a joint research agreement that was in effect before the invention of this application was made.

Ethylene, ethane, propylene, propane, and/or heavier hydrocarbons can be recovered from a variety of gases, such as natural gas, refinery gas, and synthetic gas streams obtained from other hydrocarbon materials such as coal, crude oil, naphtha, oil shale, tar sands, and lignite. Natural gas usually has a major proportion of methane and ethane, i.e., methane and ethane together comprise at least 50 mole percent of the gas. The gas also contains relatively lesser amounts of heavier hydrocarbons such as propane, butanes, pentanes, and the like, as well as hydrogen, nitrogen, carbon dioxide, and/or other gases. The recovered ethylene, ethane, propylene, propane, and/or heavier hydrocarbons are generally recovered as a mixed product by a gas processing plant, whereupon the mixed hydrocarbon product is then sent elsewhere for further processing and/or use as feedstock for chemical conversion and/or fuel production processes.

The present invention is generally concerned with the separation of such mixed hydrocarbon streams into a fraction containing the more volatile hydrocarbon components and a fraction containing the less volatile hydrocarbon components. Such separation is often advantageous because one or both of the products is more valuable when separated from the other product. For example, separating (deethanizing) the ethane from the natural gas liquids (NGL) produced in a gas processing plant would allow the ethane to be used as a premium feedstock for an ethylene cracking process, making it more valuable than it is as a part of the NGL stream. This separate ethane product could also be more valuable based on its gaseous fuel value than it is as part of the NGL stream when there is an over-supply of ethane in the market.

The present invention is a novel means of fractionating hydrocarbon streams that combines what heretofore have been individual equipment items into a common housing, thereby reducing both the plot space requirements and the capital cost of the addition. Surprisingly, applicants have found that the more compact arrangement also significantly reduces the power consumption required to achieve a given recovery level, thereby increasing the process efficiency and reducing the operating cost of the facility. In addition, the more compact arrangement also eliminates much of the piping used to interconnect the individual equipment items in traditional plant designs, further reducing capital cost and also eliminating the associated flanged piping connections. Since piping flanges are a potential lead source for hydrocarbons (which are volatile organic compounds, VOCs, that contribute to greenhouse gases and may also be precursors to atmospheric ozone formation), eliminating these flanges reduces the potential for atmospheric emissions that may damage the environment.

For a better understanding of the present invention, reference is made to the following examples and drawings. Referring to the drawings.

In the following explanation of the above figures, tables are provided summarizing flow rates calculated for representative process conditions. In the tables appearing herein, the values for flow rates (in moles per hour) have been rounded to the nearest whole number for convenience. The total stream rates shown in the tables include all non-hydrocarbon components and hence are generally larger than the sum of the stream flow rates for the hydrocarbon components. Temperatures indicated are approximate values rounded to the nearest degree. It should also be noted that the process design calculations performed for the purpose of comparing the processes depicted in the figures are based on the assumption of no heat leak from (or to) the surroundings to (or from) the process. The quality of commercially available insulating materials makes this a very reasonable assumption and one that is typically made by those skilled in the art.

For convenience, process parameters are reported in both the traditional British units and in the units of the Système International d'Unités (SI). The molar flow rates given in the tables may be interpreted as either pound moles per hour or kilogram moles per hour. The energy consumptions reported as horsepower (HP) and/or thousand British Thermal Units per hour (MBTU/Hr) correspond to the stated molar flow rates in pound moles per hour. The energy consumptions reported as kilowatts (kW) correspond to the stated molar flow rates in kilogram moles per hour.

DESCRIPTION OF THE PRIOR ART

Figure 1:
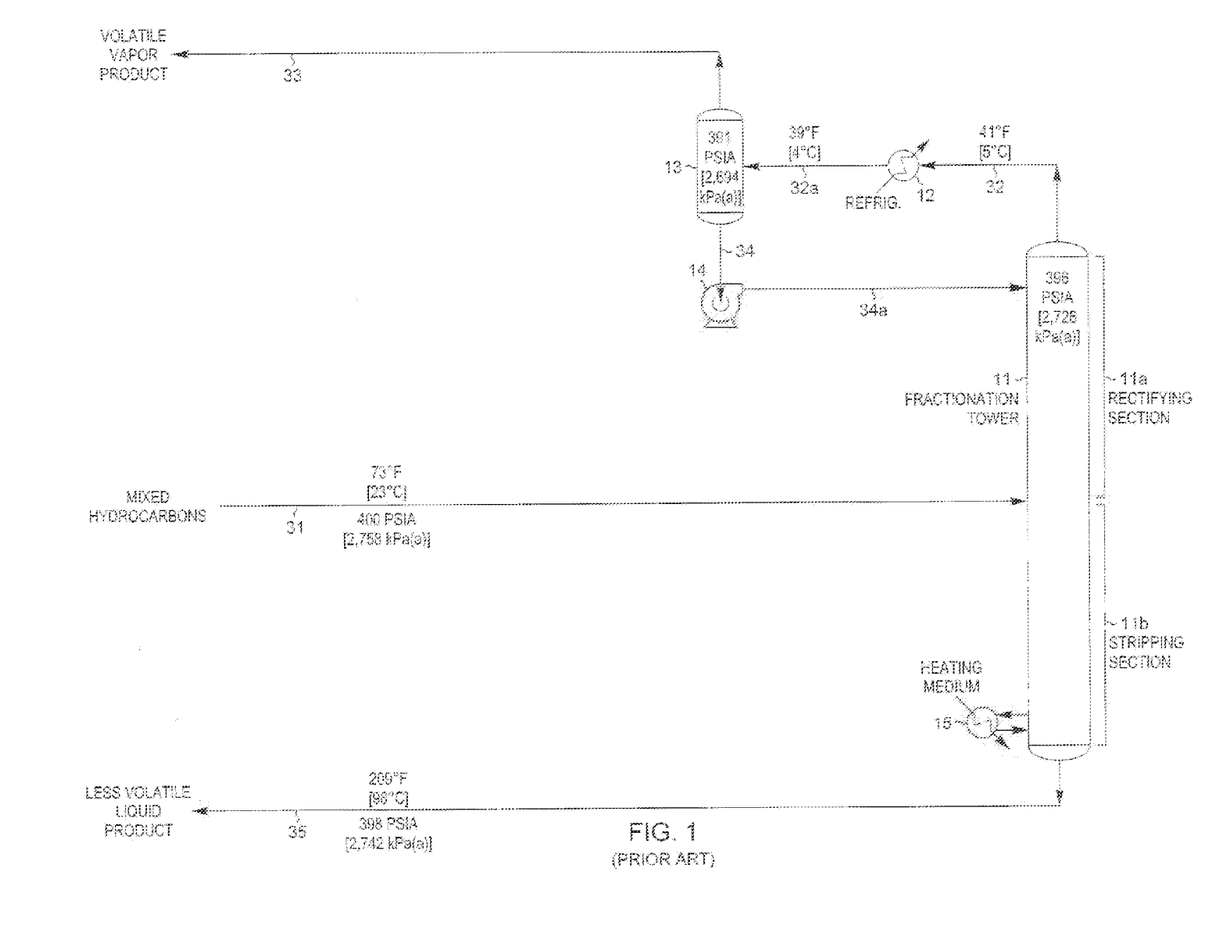
FIG. 1 is a flow diagram of a prior art hydrocarbon fractionation plant similar to that shown in FIG. 2 of "New NGL-Recovery Process Provides Viable Alternative", Huebel, Robert R. and Malsam, Michael G., Oil & Gas Journal, Jan. 9, 2012.

FIG. 1 is a process flow diagram showing the design of a processing plant to remove $C_2$ components and lighter components from an NGL stream using a prior art process. In this simulation of the process, the mixed hydrocarbon liquids enter the plant at 73° F.[23° C.] and 400 psia [2,758 kPa(a)] as stream 31 which is directed to a mid-column feed point on fractionation tower (deethanizer) 11.

The deethanizer in tower 11 is a conventional distillation column containing a plurality of vertically spaced trays, one or more packed beds, or some combination of trays and packing. As is often the case, the fractionation tower may consist of two sections, an upper rectifying section 11a and a lower stripping section 11b. The upper rectifying section 11a contains trays and/or packing and provides the necessary contact between the vapor rising from the lower distillation or deethanizing section 11b and a liquid stream (reflux) to remove the $C_3$ components and heavier components from the vapor. The lower stripping (deethanizing) section 11b also contains trays and/or packing and provides the necessary contact between the liquids falling downward and the vapors rising upward. Stripping section 11b also includes at least one reboiler (such as the reboiler 15) which heats and vaporizes a portion of the liquids flowing down the column to provide the stripping vapors which flow up the column to strip the liquid product, stream 35, of $C_2$ components and lighter components. Liquid product stream 35 exits the bottom of the tower at 209° F.[98° C.], based on a typical specification of an ethane to propane ratio of 0.020:1 on a molar basis in the bottom product, and contains essentially only the less volatile components that were in NGL feed stream 31, which in this case are the propane and heavier components.

The column overhead vapor (stream 32) is withdrawn from the top of deethanizer 11 at 41° F.[5° C.] and partially condensed (stream 32a as it is cooled to 39° F.[4° C.] in heat exchanger 12 using a refrigerant. The operating pressure (391 psia [2,694 kPa(a)]) in reflux separator 13 is maintained slightly below the operating pressure (396 psia [2,728 kPa (a)]) of deethanizer 11. This provides the driving force which causes overhead vapor stream 32 to flow through reflux condenser 12 and thence into the reflux separator 13 wherein the condensed liquid (stream 34) is separated from the uncondensed vapor (stream 33). The liquid stream 34 from reflux separator 13 is pumped by reflux pump 14 to a pressure slightly above the operating pressure of deethanizer 11, and stream 34a is then supplied as cold top column feed (reflux) to deethanizer 11. This cold fluid reflux absorbs and condenses the $C_3$ components and heavier components in the vapors rising up in rectifying section 11a of deethanizer 11. Vapor product stream 33 contains the more volatile components that were in NGL feed stream 31, which in this case are the ethane and lighter components (based on a typical specification of 0.75% propane in the ethane product on a molar basis).

A summary of stream flow rates and energy consumption for the process illustrated in FIG. 1 is set forth in the following table:

TABLE I (FIG. 1)
Stream Flow Summary—Lb. Moles/Hr [kg moles/Hr]

| Stream | Methane | Ethane | Propane | Butanes | Pentanes+ | Total |
|---|---|---|---|---|---|---|
| 31 | 15 | 1,482 | 681 | 329 | 192 | 2,727 |
| 32 | 20 | 3,444 | 19 | 0 | 0 | 3,530 |
| 34 | 5 | 1,975 | 15 | 0 | 0 | 2,015 |
| 33 | 15 | 1,469 | 4 | 0 | 0 | 1,515 |
| 35 | 0 | 13 | 677 | 329 | 192 | 1,212 |

| Recoveries* | | |
|---|---|---|
| Propane | 99.35% | |
| Butanes+ | 100.00% | |
| Power | | |
| Refrigerant Compression | 1,027 HP | [ 1,688 kW] |
| Utility Heat | | |
| Deethanizer Reboiler | 18,020 MBTU/Hr | [ 11,641 kW] |

*(Based on un-rounded flow rates)

DESCRIPTION OF THE INVENTION

Figure 2:
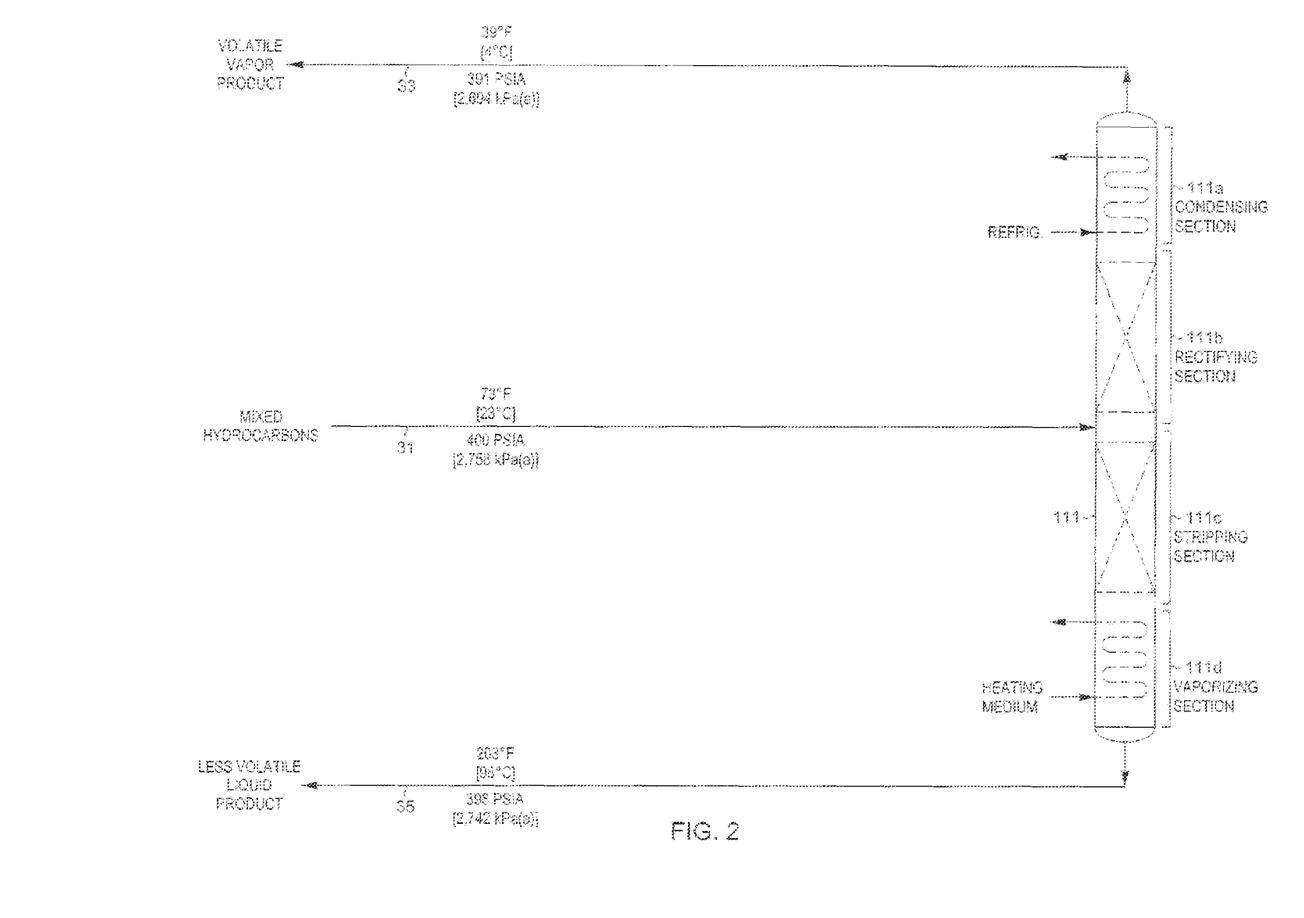
FIG. 2 is a flow diagram of a hydrocarbon fractionation plant in accordance with the present invention.

FIG. 2 illustrates a flow diagram of a process in accordance with the present invention. The NGL stream composition and conditions considered in the process presented in FIG. 2 are the same as those in FIG. 1. Accordingly, the FIG. 2 process can be compared with that of the FIG. 1 process to illustrate the advantages of the present invention.

In the process illustrated in FIG. 2, mixed hydrocarbon liquids stream 31 at 73° F. [23° C.] and 400 psia [2,758 kPa(a)] is directed to processing assembly 111, entering between an absorbing means inside rectifying section 111b and a mass transfer means inside stripping section 111c. The liquids leaving the lower region of the absorbing means combine with the liquid portion (if any) of feed stream 31, and the combined liquids enter the upper region of the mass transfer means. The vapors leaving the upper region of the mass transfer means combine with the vapor portion (if any) of feed stream 31, and the combined vapors enter the lower region of the absorbing means.

A heat and mass transfer means is located below the mass transfer means inside vaporizing section 111d of processing assembly 111. The heat and mass transfer means may be comprised of a tin and tube type heat exchanger, a plate type heat exchanger, a brazed aluminum type heat exchanger, or other type of heat transfer device, including multi-pass and/or multi-service heat exchangers. The heat and mass transfer means is configured to provide heat exchange between a heating medium flowing through one pass of the heat and mass transfer means and a distillation liquid stream flowing downward from the lower region of the mass transfer means, so that the distillation liquid stream is heated. As the distillation liquid stream is heated, a portion of it is vaporized to form stripping vapors that rise upward to the mass transfer means as the remaining liquid continues flowing downward through the heat and mass transfer means. The heat and mass transfer means provides continuous contact between the stripping vapors and the distillation liquid stream so that it also functions to provide mass transfer between the vapor and liquid phases, stripping the liquid product stream 35 of ethane and lighter components. The stripping vapors produced in the heat and mass transfer means continue upward to the mass transfer means in stripping section 111c to provide partial stripping of the lighter components in the liquids flowing downward from the upper part of processing assembly 111.

Another heat and mass transfer means is located above the absorbing means, inside condensing section 111a of processing assembly 111. This heat and mass transfer means may also be comprised of a tin and tube type heat exchanger, a plate type heat exchanger, a brazed aluminum type heat exchanger, or other type of heat transfer device, including multi-pass and/or multi-service heat exchangers. The heat and mass transfer means is configured to provide heat exchange between a refrigerant stream flowing through one pass of the heat and mass transfer means and the distillation vapor stream arising from the upper region of the absorbing means flowing upward through the other pass, so that the distillation vapor stream is cooled by the refrigerant. As the distillation vapor stream is cooled, a portion of it is condensed and falls downward while the remaining distillation vapor stream continues flowing upward through the heat and mass transfer means. The heat and mass transfer means provides continuous contact between the condensed liquid and the distillation vapor stream so that it also functions to provide mass transfer between the vapor and liquid phases, thereby absorbing propane and heavier components from the distillation vapor stream to rectify it. The condensed liquid is collected from the bottom of the heat and mass transfer means and directed to the upper region of the absorbing means inside rectifying section 111b to provide partial rectification of the heavier components in the vapors flowing upward from the lower part of processing assembly 111.

The absorbing means inside rectifying section 111b and the mass transfer means inside stripping section 111c each consist of a plurality of vertically spaced trays, one or more packed beds, or some combination of trays and packing. The trays and/or packing in rectifying section 111b and stripping section 111c provide the necessary contact between the vapors rising upward and liquid falling downward. The liquid portion (if any) of feed stream 31 commingles with liquids falling downward from rectifying section 111b and the combined liquids continue downward into stripping section 111c, which vaporizes and strips the ethane and lighter components from these liquids. The vapors arising from stripping section 111c commingle with the vapor portion (if any) of feed stream 31 and the combined vapors rise upward through rectifying section 111b, to be contacted with the cold liquid falling downward to condense and absorb most of the $C_3$ components and heavier components from these vapors.

The distillation liquid flowing downward from the heat and mass transfer means in vaporizing section 111d inside processing assembly 111 has been stripped of ethane and lighter components. The resulting liquid product (stream 35) exits the lower region of vaporizing section 111d at 208° F. [98° C.], based on a typical specification of a ethane to propane ratio of 0.020:1 on a molar basis in the bottom product, and leaves processing assembly 111. This liquid product contains the less volatile components that were in NGL feed stream 31, which in this case are the propane and heavier components. The distillation vapor stream 33 arising from condensing section 111a leaves processing assembly 111 at 39° F.[4° C.] and 391 psia [2,694 kPa(a)], based on a typical specification of 0.75% propane in the ethane product on a molar basis, as the volatile vapor product containing the more volatile components that were in NGL feed stream 31, which in this case are the ethane and lighter components.

A summary of stream flow rates and energy consumption for the process illustrated in FIG. 2 is set forth in the following table:

TABLE II (FIG. 2)
Stream Flow Summary—Lb. Moles/Hr [kg moles/Hr]

| Stream | Methane | Ethane | Propane | Butanes | Pentanes+ | Total |
|---|---|---|---|---|---|---|
| 31 | 15 | 1,482 | 681 | 329 | 192 | 2,727 |
| 33 | 15 | 1,469 | 4 | 0 | 0 | 1,515 |
| 35 | 0 | 13 | 677 | 329 | 192 | 1,212 |

Recoveries*

| | |
|---|---|
| Propane | 99.35% |
| Butanes+ | 100.00% |
| Power | |

TABLE II-continued (FIG. 2)
Stream Flow Summary—Lb. Moles/Hr [kg moles/Hr]

| | | |
|---|---|---|
| Refrigerant Compression Utility Heat | 952 HP | [ 1,565 kW] |
| Deethanizer Reboiler | 17.860 MBTU/Hr | [ 11,538 kW] |

*(Based on un-rounded flow rates)

A comparison of Tables I and II shows that the present invention maintains the same recoveries as the prior art. However, further comparison of Tables I and II shows that the product yields were achieved using significantly less power than the prior art. In terms of the recovery efficiency (defined by the quantity of propane recovered per unit of power), the present invention represents more than a 7% improvement over the prior art of the FIG. 1 process. The present invention also uses nearly 1% less utility heat than the prior art of the FIG. 1 process.

The improvement in recovery efficiency provided by the present invention over that of the prior art of the FIG. 1 process is primarily due to two factors. First, using the heat and mass transfer means in condensing section 111a to simultaneously cool the distillation vapor stream and condense the heavier hydrocarbon components from it provides more efficient rectification than using reflux in a conventional distillation column. As a result, the $C_3$ components and heavier hydrocarbon components can be removed from the distillation vapor stream using less refrigeration than is possible using conventional mass transfer equipment and conventional heat transfer equipment like the prior art of the FIG. 1 process.

Second, using the heat and mass transfer means in vaporizing section 111d to simultaneously heat the distillation liquid stream leaving the mass transfer means in stripping section 111e while allowing the resulting vapors to contact the liquid and strip its volatile components is more efficient than using a conventional distillation column with external reboilers. The volatile components are stripped out of the liquid continuously, reducing the concentration of the volatile components in the stripping vapors more quickly and thereby improving the stripping efficiency for the present invention.

The present invention also offers at least two additional advantages over the prior art. First, the compact arrangement of processing assembly 111 of the present invention replaces five separate equipment items in the prior art (fractionation tower 11, reflux condenser 12, reflux separator 13, reflux pump 14, and reboiler 15) with a single equipment item (processing assembly 111 in FIG. 2 of the present invention). This reduces the plot space requirements and eliminates the interconnecting piping, reducing the capital cost of the processing plant. Second, elimination of the interconnecting piping means that a processing plant using the present invention has far fewer flanged connections compared to the prior art, reducing the number of potential leak sources in the plant. Hydrocarbons are volatile organic compounds (VOCs), some of which are classified as greenhouse gases and some of which may be precursors to atmospheric ozone formation, which means the present invention reduces the potential for atmospheric releases that may damage the environment.

OTHER EMBODIMENTS

Figure 3:
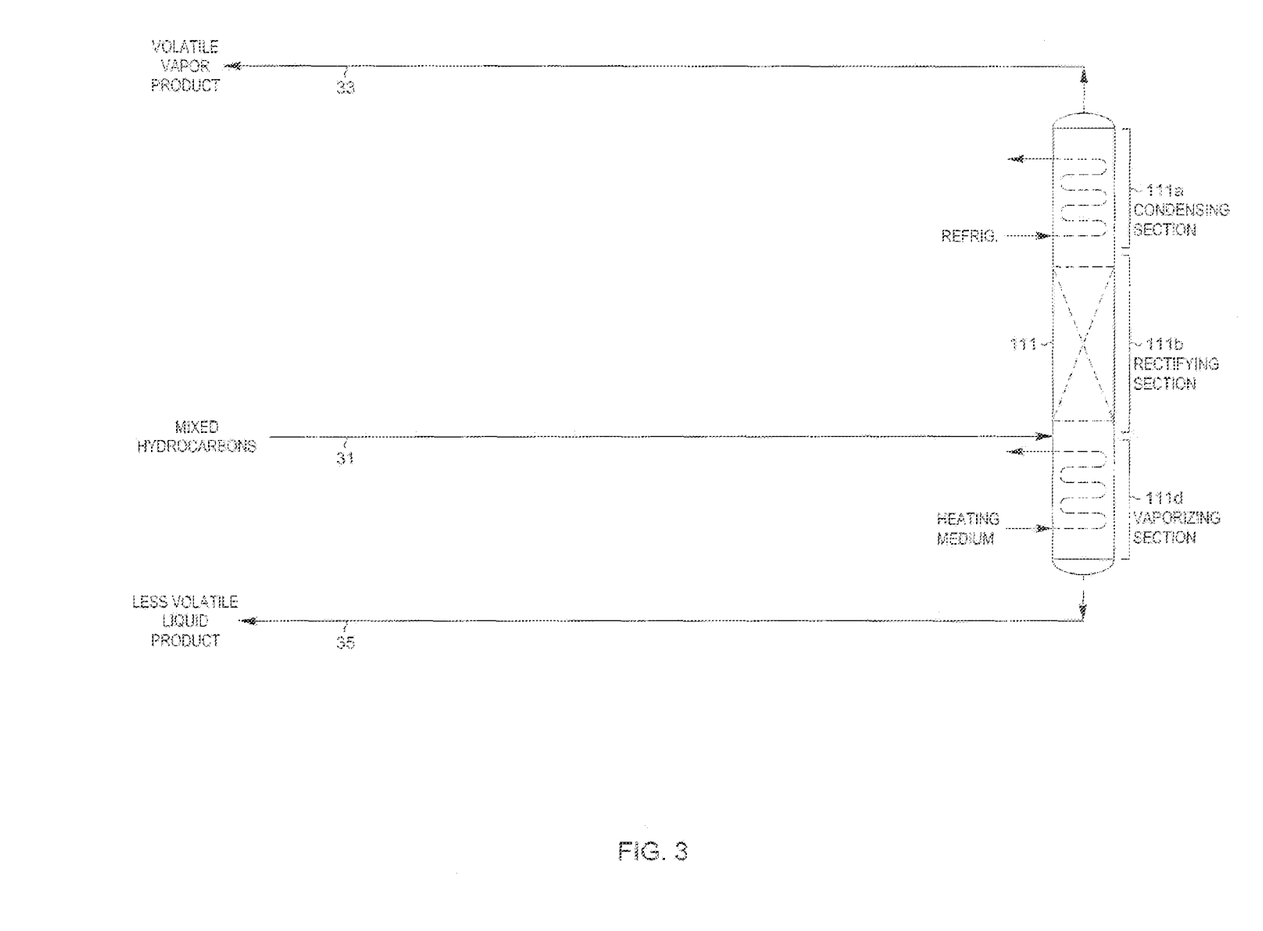
FIGS. 3 through 9 are flow diagrams illustrating alternative means of application of the present invention to a hydrocarbon stream.
Figure 4:
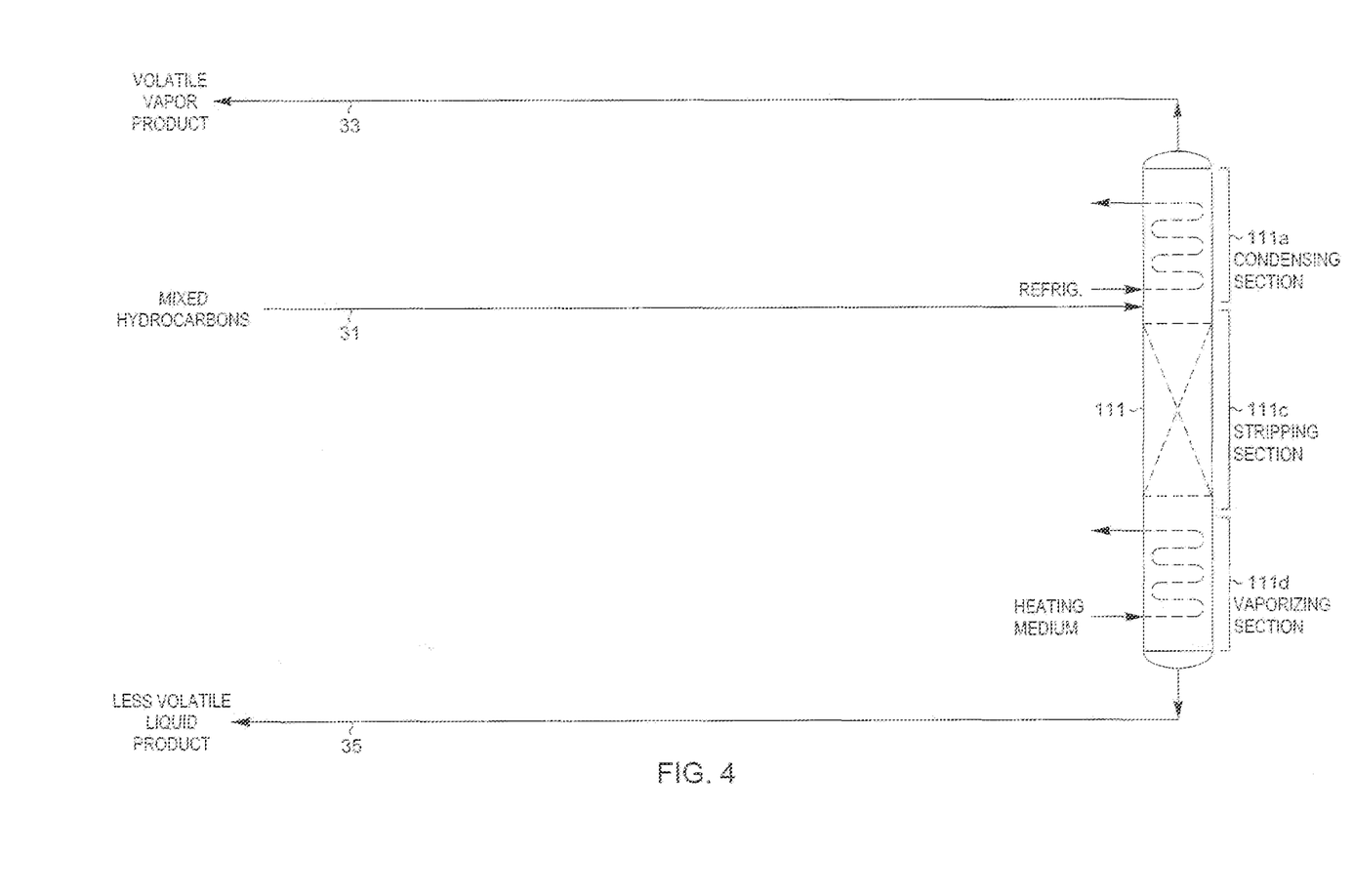
Figure 5:
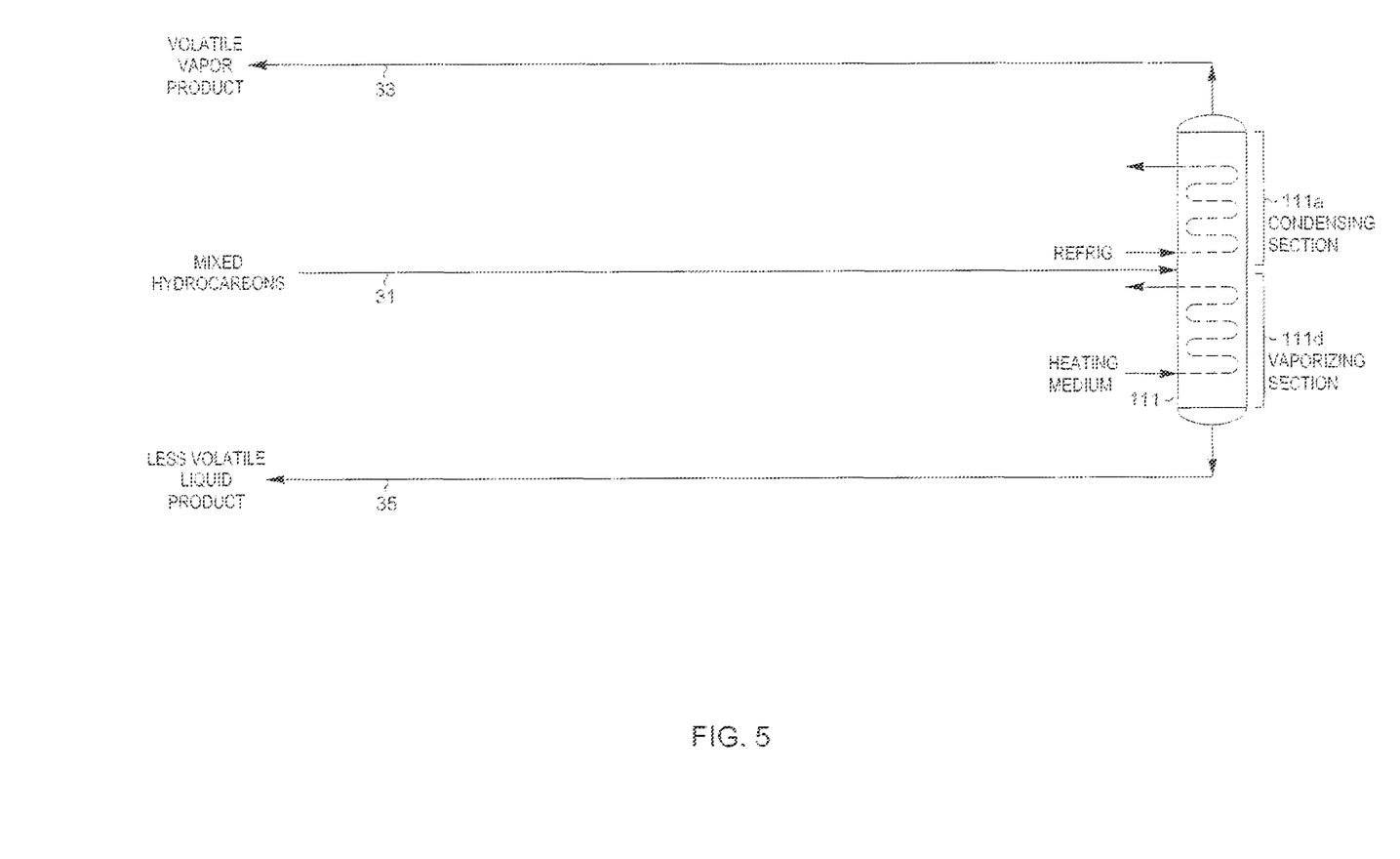

Some circumstances may favor not providing a mass transfer means above vaporizing section 111d, allowing the elimination of stripping section 111c. In such cases, the liquid portion of feed stream 31 and the liquids from either rectifying section 111b (FIG. 3) or condensing section 111a (FIG. 5) flow directly to vaporizing section 111d. Likewise, some circumstances may favor not providing an absorbing means below condensing section 111a, allowing the elimination of rectifying section 111b. In such cases, the liquid condensed from the distillation vapor entering condensing section 111a is directed to either stripping section 111c (FIG. 4) or vaporizing section 111d (FIG. 5).

Figure 6:
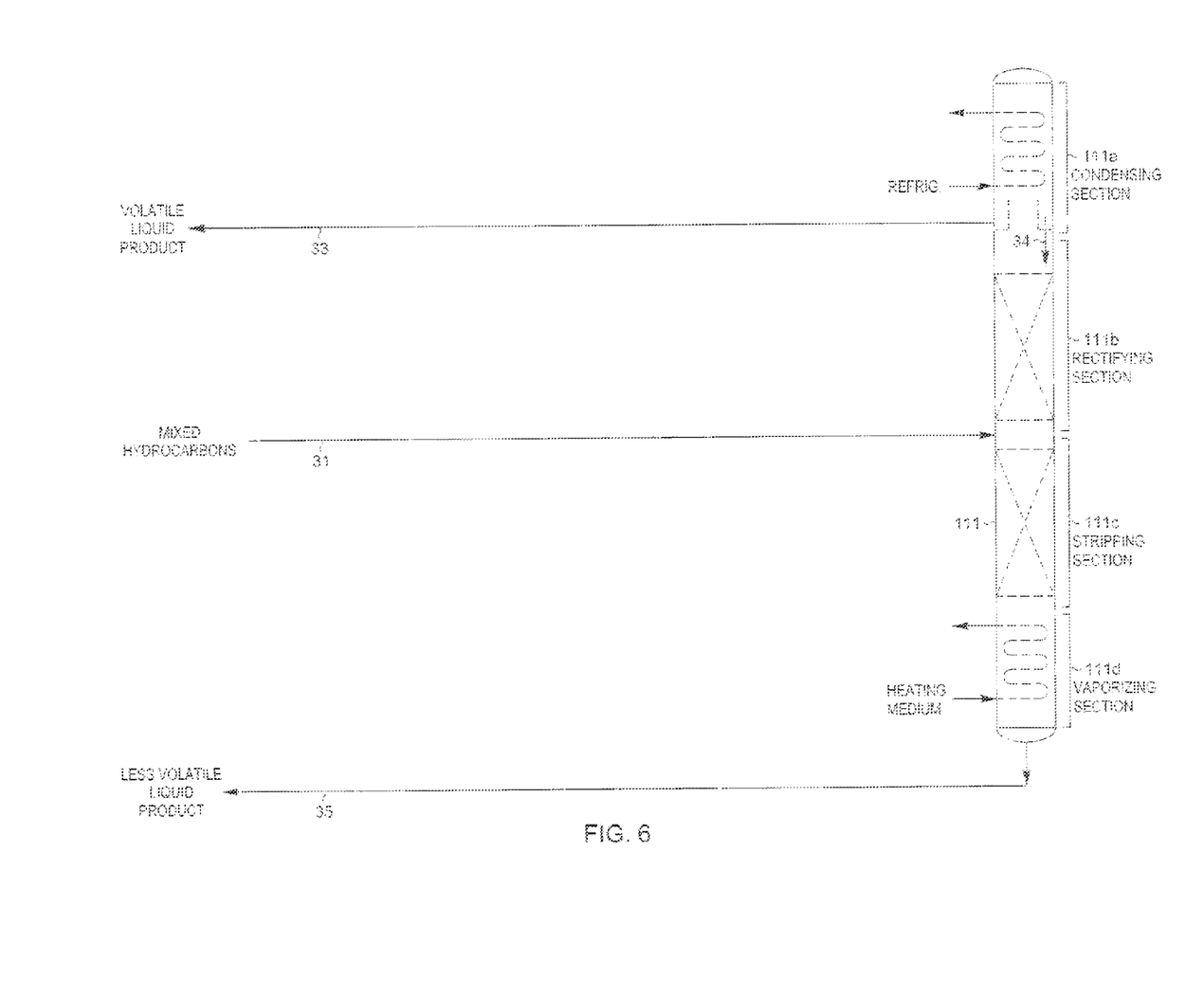
Figure 7:
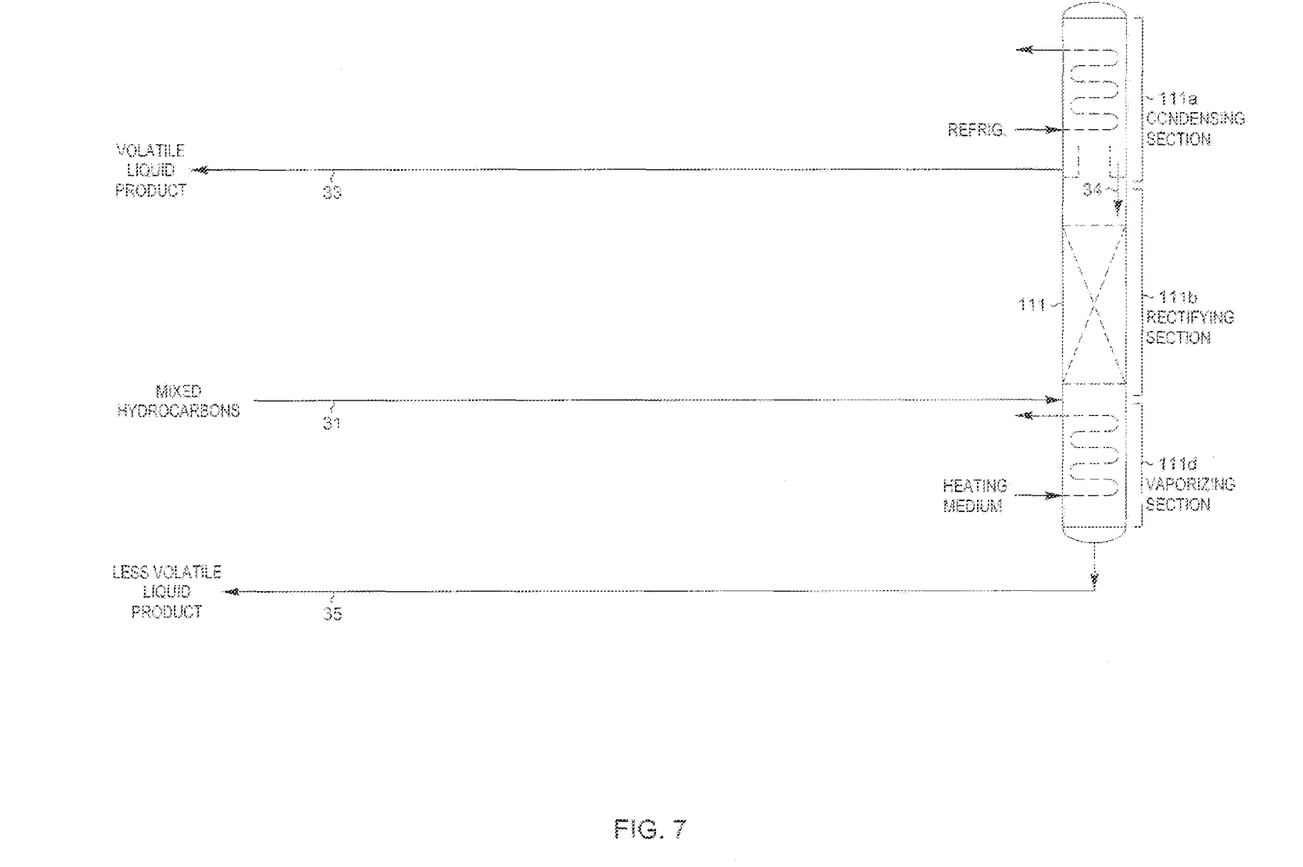
Figure 8:
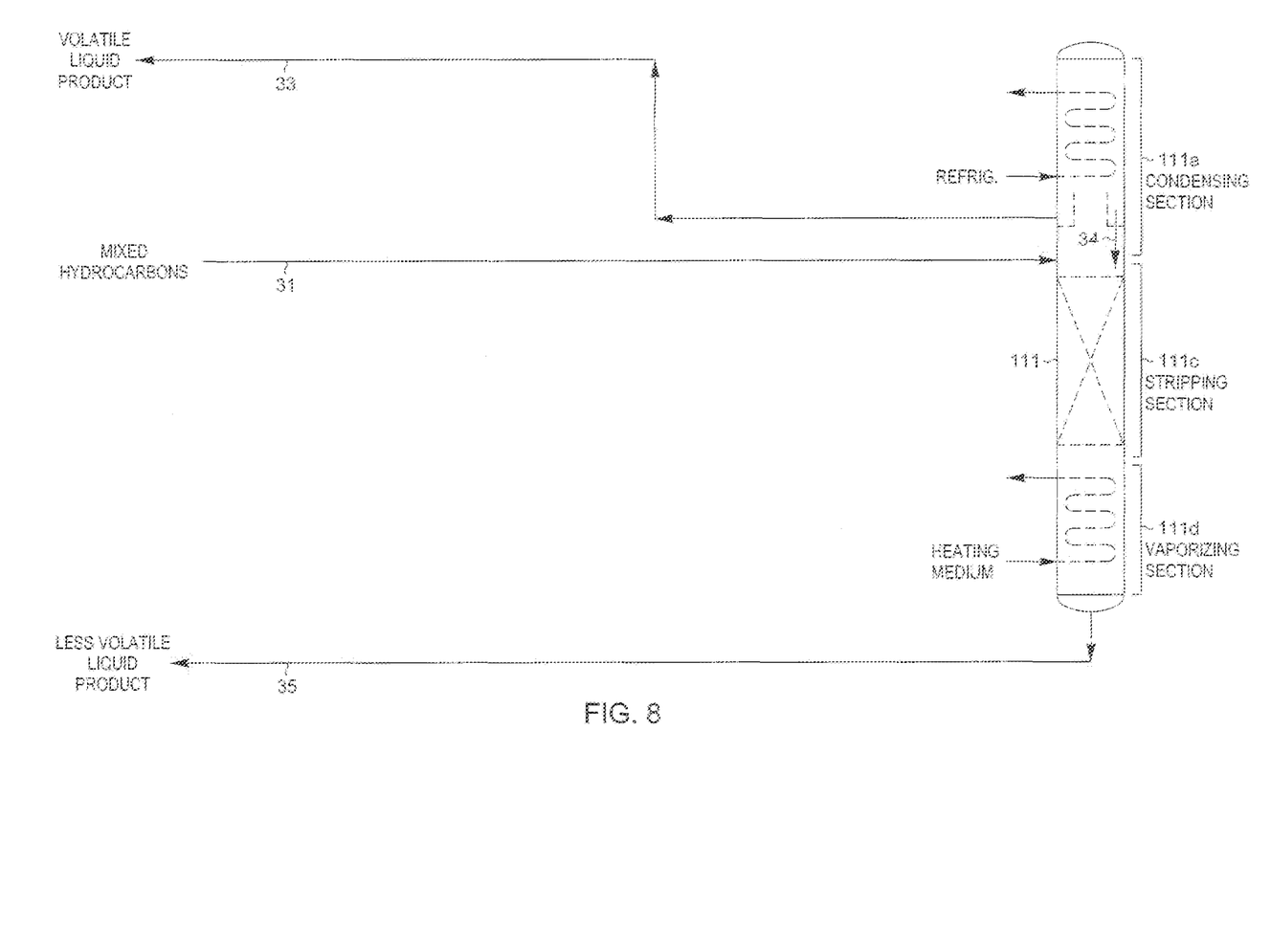
Figure 9:
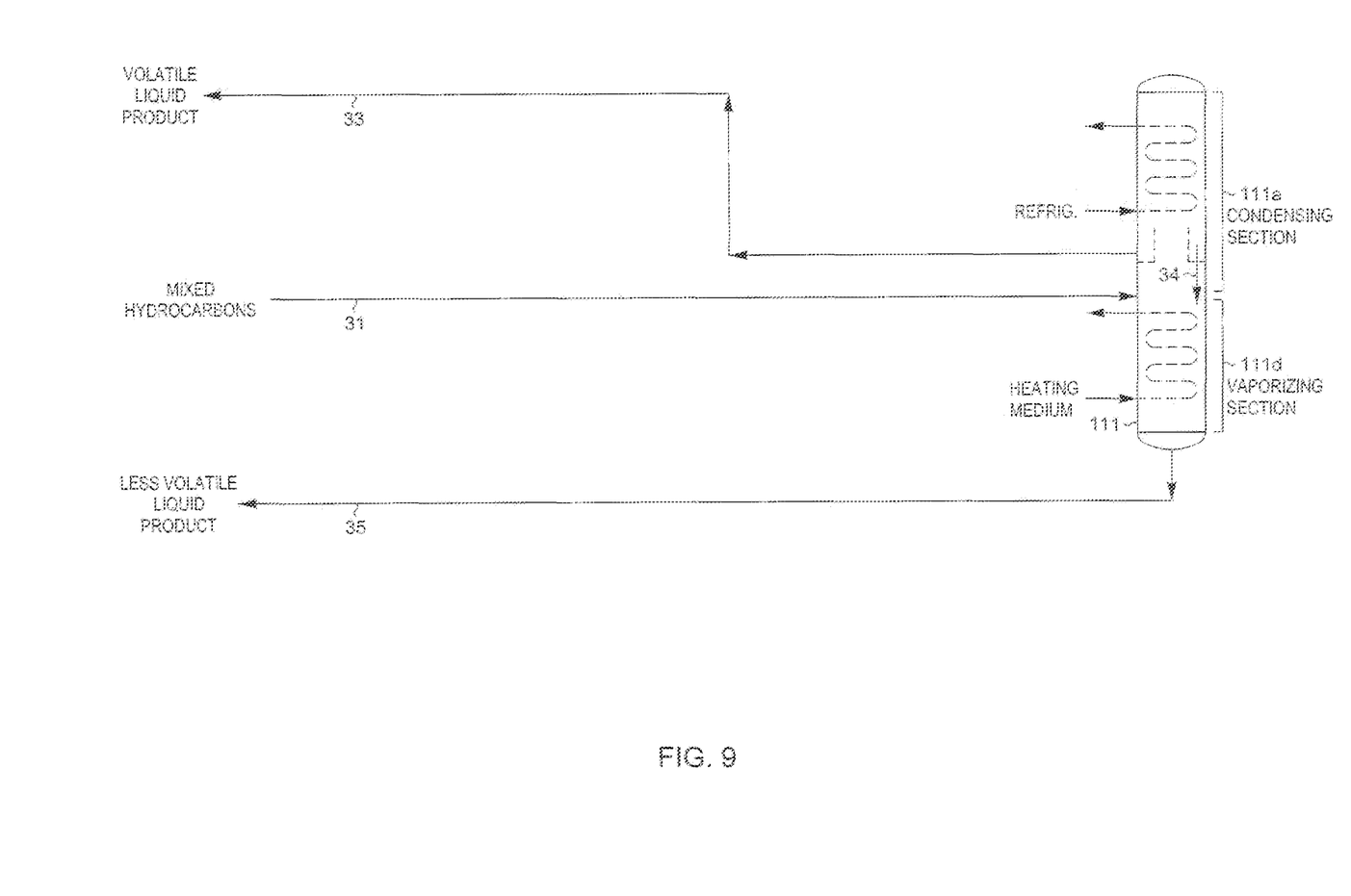

Some circumstances may favor producing the more volatile product as a liquid stream rather than a vapor stream. In such cases, the heat and mass transfer means inside condensing section 111a can be configured to totally condense either the distillation vapor stream arising from the absorbing means inside rectifying section 111b (FIGS. 6 and 7) or the vapor portion of feed stream 31 combined with the distillation vapor stream from either stripping section 111c (FIG. 8) or vaporizing section 111d (FIG. 9). A liquid collecting means can then be used to direct a portion of the condensed liquid (reflux stream 34) to the upper region of the absorbing means in rectifying section 111b (FIGS. 6 and 7), to stripping section 111c (FIG. 8), or to vaporizing section 111d (FIG. 9), with the remainder leaving processing assembly 111 as volatile liquid product 33. Again, some circumstances may favor not providing a mass transfer means above vaporizing section 111d, allowing the elimination of stripping section 111c. In such cases, the liquid portion of feed stream 31 and either the liquids from rectifying section 111b (FIG. 7) or reflux stream 34 from condensing section 111a (FIG. 9) flow directly to vaporizing section 111d. Likewise, some circumstances may favor not providing an absorbing means below condensing section 111a, allowing the elimination of rectifying section 111b. In such cases, reflux stream 34 from condensing section 111a is directed to either stripping section 111c (FIG. 8) or vaporizing section 111d (FIG. 9).

The present invention can be used to effect the desired separation between any components of different volatilities in a liquid hydrocarbon stream as required by the particular circumstances by appropriate adjustment of the operating conditions. For instance, the present invention can be used to separate $C_3$ components and lighter components for a liquefied petroleum gas (LPG) stream, so that the $C_4$ components and heavier components remain in the less volatile liquid product. The present invention can also be used to process a vapor hydrocarbon stream or a hydrocarbon stream or a hydrocarbon stream containing a mixture of liquid and vapor.

While there have been described what are believed to be preferred embodiments of the invention, those skilled in the art will recognize that other and further modifications may be made thereto, e.g. to adapt the invention to various conditions, types of feed, or other requirements without departing from the spirit of the present invention as defined by the following claims.

We claim:

1. A process for the separation of a mixed hydrocarbon stream containing at least a lighter hydrocarbon component and a heavier hydrocarbon component into a volatile fraction containing a major portion of said lighter hydrocarbon component and a relatively less volatile fraction containing a major portion of said heavier hydrocarbon component wherein
   (1) said mixed hydrocarbon stream is supplied as a feed between a first heat and mass transfer means and a second heat and mass transfer means housed in a processing assembly, said first heat and mass transfer means being located above said second heat and mass transfer means;
   (2) a first distillation vapor stream is collected from an upper region of said second heat and mass transfer means and combined with any vapor portion of said feed to form a combined vapor stream;
   (3) said combined vapor stream is cooled in said first heat and mass transfer means to simultaneously condense the less volatile components from said combined vapor stream, thereby forming a first distillation liquid stream and a second distillation vapor stream, whereupon said second distillation vapor stream is discharged from said processing assembly as said volatile fraction;
   (4) said first distillation liquid stream is collected from a lower region of said first heat and mass transfer means and combined with any liquid portion of said feed to form a combined liquid stream;
   (5) said combined liquid stream is heated in said second heat and mass transfer means to simultaneously strip the more volatile components from said combined liquid stream, thereby forming said first distillation vapor stream and a second distillation liquid stream, whereupon said second distillation liquid stream is discharged from said processing assembly as said relatively less volatile fraction; and
   (6) a control means is adapted to maintain the temperature of said volatile fraction at a temperature whereby the major portion of said heavier hydrocarbon component is recovered in said relatively less volatile fraction and to maintain the temperature of said relatively less volatile fraction at a temperature whereby the major portion of said lighter hydrocarbon component is recovered in said volatile fraction.

2. The process according to claim 1 wherein
   (1) an absorbing means is housed in said processing assembly below said first heat and mass transfer means and above said second heat and mass transfer means;
   (2) said combined vapor stream and said first distillation liquid stream are directed to said absorbing means to condense the less volatile components from said combined vapor stream, thereby forming a third distillation liquid stream and a third distillation vapor stream;
   (3) said third distillation vapor stream is collected from an upper region of said absorbing means and cooled in said first heat and mass transfer means to simultaneously condense the less volatile components from said third distillation vapor stream, thereby forming said first distillation liquid stream and said second distillation vapor stream; and
   (4) said third distillation liquid stream is collected from a lower region of said absorbing means and combined with said any liquid portion of said feed to form said combined liquid stream.

3. The process according to claim 1 wherein
   (1) a mass transfer means is housed in said processing assembly below said first heat and mass transfer means and above said second heat and mass transfer means;
   (2) said combined liquid stream and said first distillation vapor stream are directed to said mass transfer means to strip the more volatile components from said combined liquid stream, thereby forming a third distillation liquid stream and a third distillation vapor stream;
   (3) said third distillation vapor stream is collected from an upper region of said mass transfer means and combined with said any vapor portion of said feed to form said combined vapor stream; and (4) said third distillation liquid stream is collected from a lower region of said mass transfer means and heated in said second heat and mass transfer means to simultaneously strip the more volatile components from said third distillation liquid stream, thereby forming said first distillation vapor stream and said second distillation liquid stream.

4. The process according to claim 2 wherein
(1) a mass transfer means is housed in said processing assembly below said absorbing means and above said second heat and mass transfer means;
(2) said combined liquid stream and said first distillation vapor stream are directed to said mass transfer means to strip the more volatile components from said combined liquid stream, thereby forming a fourth distillation liquid stream and a fourth distillation vapor stream;
(3) said fourth distillation vapor stream is collected from an upper region of said mass transfer means and combined with said any vapor portion of said feed to form said combined vapor stream; and
(4) said fourth distillation liquid stream is collected from a lower region of said mass transfer means and heated in said second heat and mass transfer means to simultaneously strip the more volatile components from said fourth distillation liquid stream, thereby forming said first distillation vapor stream and said second distillation liquid stream.

5. The process according to claim 1 wherein
(1) said combined vapor stream is cooled in said first heat and mass transfer means sufficiently to substantially condense it, thereby forming a condensed stream; and
(2) said condensed stream is divided into said first distillation liquid stream and a third distillation liquid stream, whereupon said third distillation liquid stream is discharged from said processing assembly as said volatile fraction.

6. The process according to claim 2 wherein
(1) said third distillation vapor stream is cooled in said first heat and mass transfer means sufficiently to substantially condense it, thereby forming a condensed stream; and
(2) said condensed stream is divided into said first distillation liquid stream and a fourth distillation liquid stream, whereupon said fourth distillation liquid stream is discharged from said processing assembly as said volatile fraction.

7. The process according to claim 3 wherein
(1) said combined vapor stream is cooled in said first heat and mass transfer means sufficiently to substantially condense it, thereby forming a condensed stream; and
(2) said condensed stream is divided into said first distillation liquid stream and a fourth distillation liquid stream, whereupon said fourth distillation liquid stream is discharged from said processing assembly as said volatile fraction.

8. The process according to claim 4 wherein
(1) said third distillation vapor stream is cooled in said first heat and mass transfer means sufficiently to substantially condense it, thereby forming a condensed stream; and
(2) said condensed stream is divided into said first distillation liquid stream and a fifth distillation liquid stream, whereupon said fifth distillation liquid stream is discharged from said processing assembly as said volatile fraction.

* * * * *

UNITED STATES PATENT AND TRADEMARK OFFICE
CERTIFICATE OF CORRECTION

PATENT NO. : 9,790,147 B2
APPLICATION NO. : 14/462069
DATED : October 17, 2017
INVENTOR(S) : Joe T. Lynch et al.

Page 1 of 1

It is certified that error appears in the above-identified patent and that said Letters Patent is hereby corrected as shown below:

In the Specification

Column 3:
Line 8, "(stream 32a" should read --(stream 32a)--.

Column 4:
Line 9, "tin" should read --fin--; and
Line 58, "tin" should read --fin--.

Column 6:
Line 36, "111$e$" should read --111$c$--.

Signed and Sealed this
Thirtieth Day of January, 2018

Joseph Matal
*Performing the Functions and Duties of the
Under Secretary of Commerce for Intellectual Property and
Director of the United States Patent and Trademark Office*